United States Patent [19]

Cottone, Jr. et al.

[11] Patent Number: 5,184,625
[45] Date of Patent: Feb. 9, 1993

[54] BIOPSY FORCEPS DEVICE HAVING IMPROVED HANDLE

[75] Inventors: Robert J. Cottone, Jr., Fort Lauderdale, Fla.; Joseph J. Kopp, Jr., Atlanta; David S. Rowley, Smyrna, both of Ga.

[73] Assignee: Cordis Corporation, Miami, Fla.

[21] Appl. No.: 869,393

[22] Filed: Apr. 16, 1992

[51] Int. Cl.⁵ .......................................... A61B 10/00
[52] U.S. Cl. .................................. 128/751; 606/171; 606/206
[58] Field of Search ................ 606/205, 206, 207, 171; 128/751

[56] References Cited

U.S. PATENT DOCUMENTS

| | | | |
|---|---|---|---|
| 2,790,437 | 4/1957 | Moore | 128/751 |
| 4,763,668 | 8/1988 | Macek et al. | 128/751 |
| 4,763,669 | 8/1988 | Jaeger | 128/751 |
| 4,815,476 | 3/1989 | Clossick | 128/751 |
| 4,945,920 | 8/1990 | Clossick | 128/751 |

Primary Examiner—Stephen C. Pellegrino
Assistant Examiner—Gary Jackson
Attorney, Agent, or Firm—Tarolli, Sundheim & Covell

[57] ABSTRACT

A biopsy forceps device is presented herein wherein an elongated flexible hollow body portion having a lumen extending therethrough is provided with proximal and distal ends. A forceps assembly is coupled to the distal end of the body portion and the assembly includes a pair of forceps. A control wire having proximal and distal ends extends through the lumen of the body portion and is coupled at its proximal end to a handle and at its distal end to a forceps assembly. A trigger is mounted to the handle for slidable movement relative thereto between a proximal position and a distal position. A gripping device grips the proximal end of the control wire and is movable between first and second positions for respectively moving the control wire between a forceps open condition and a forceps closed condition. The gripping device is resiliently biased toward its first position. The lever arm engages and moves the gripping device from its first position to its second position against the resilient forces. A releasable locking mechanism is carried by the trigger and the lever arm to lock the gripping device in the forceps closed condition so long as the trigger is in its distal position.

10 Claims, 5 Drawing Sheets

5,184,625

BIOPSY FORCEPS DEVICE HAVING IMPROVED HANDLE

FIELD OF THE INVENTION

The present invention relates to biopsy forceps and, more particularly, to a biopsy forceps device having an improved handle.

DESCRIPTION OF THE PRIOR ART

Biopsy forceps are known in the art and are in wide use for purposes of obtaining a tissue sample. One example of the prior art takes the form of the J. P. Clossick U.S. Pat. No. 4,815,476, assigned to the same assignee as the present invention. Such a forceps device includes a handle assembly slidably mounting a trigger member thereon and an elongated coil spring guide connected to the handle assembly at the proximal end of the guide. A pair of forceps are mounted to the distal end of the guide and a stylet-control wire received within the lumen of the guide is connected at its proximal end to the trigger and at its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue sample may be examined.

The handle assembly employed in the Clossick patent discussed above is sometimes referred to as a syringe-type handle in that it includes a figure eight double finger trigger slidably mounted on the handle portion. The handle portion has a thumb ring at one end thereof. This requires the attending physician to put his thumb in the thumb ring and grasp the trigger with two fingers to achieve slidable movement of the figure-eight trigger relative to the thumb ring when actuating the forceps between open and closed positions. The handle is grasped by a physician while attempting to remove captured tissue from a body vessel and has, in practice, been found somewhat uncomfortable to many physicians requiring modifications to the handle, such as a flexible coupling permitting angular pivotal movement of the handle during such operation.

It would be desirable if a more ergonomical biopsy forceps handle be provided permitting ambidextrous use and which would fit all hand sizes. Preferably, such a handle would also include optimal human factors design permitting leverage of force applied for opening and closing the forceps. Such a handle would be comfortable for the attending physician by not requiring dedicated finger positioning and, instead, would include an in-line design with a shape that would fit the palm of a physician's hand, either left hand or right hand. Such a handle would also employ few parts and be designed for easy assembly.

SUMMARY OF THE INVENTION

In accordance with the present invention, there is provided an improved biopsy forceps device which includes an elongated flexible hollow body portion having a lumen extending therethrough and having a proximal end and a distal end. A forceps assembly is coupled to the distal end of the body portion and includes a pair of forceps. A control wire having proximal and distal ends extends through the lumen in the body portion and is coupled at its proximal end to the handle of the forceps device and at its distal end to the forceps assembly. A trigger is slidably mounted to the handle for slidable movement relative thereto between a proximate position and a distal position. A gripping device grips the proximal end of the control wire and is movable between first and second positions for respectively displacing the control wire between a forceps open condition and a forceps closed condition. A spring biases the gripping device toward its first position corresponding with the forceps open position. An actuatable lever arm engages and moves the gripping device from its first position to its second position against the resilient biasing action of the spring. A releasable locking mechanism is carried by the trigger and by the lever arm for locking the gripping device in its second position corresponding with the forceps closed condition so long as the trigger is in its distal position.

In accordance with a still further aspect of the present invention, the handle takes the form of an in-line handle with the trigger being slidably mounted thereto so that it may be easily operated, as with an operator's thumb, for releasing the locking mechanism by pulling back on the trigger so that it moves from its distal position to its proximal position causing the forceps to be actuated to an open condition.

BRIEF DESCRIPTION OF THE DRAWINGS

The foregoing and other objects of the invention will become more readily apparent from the following description of the preferred embodiment of the invention as taken in conjunction with the accompanying drawings which are a part hereof and wherein.

DESCRIPTION OF THE PREFERRED EMBODIMENT

Figure 1:
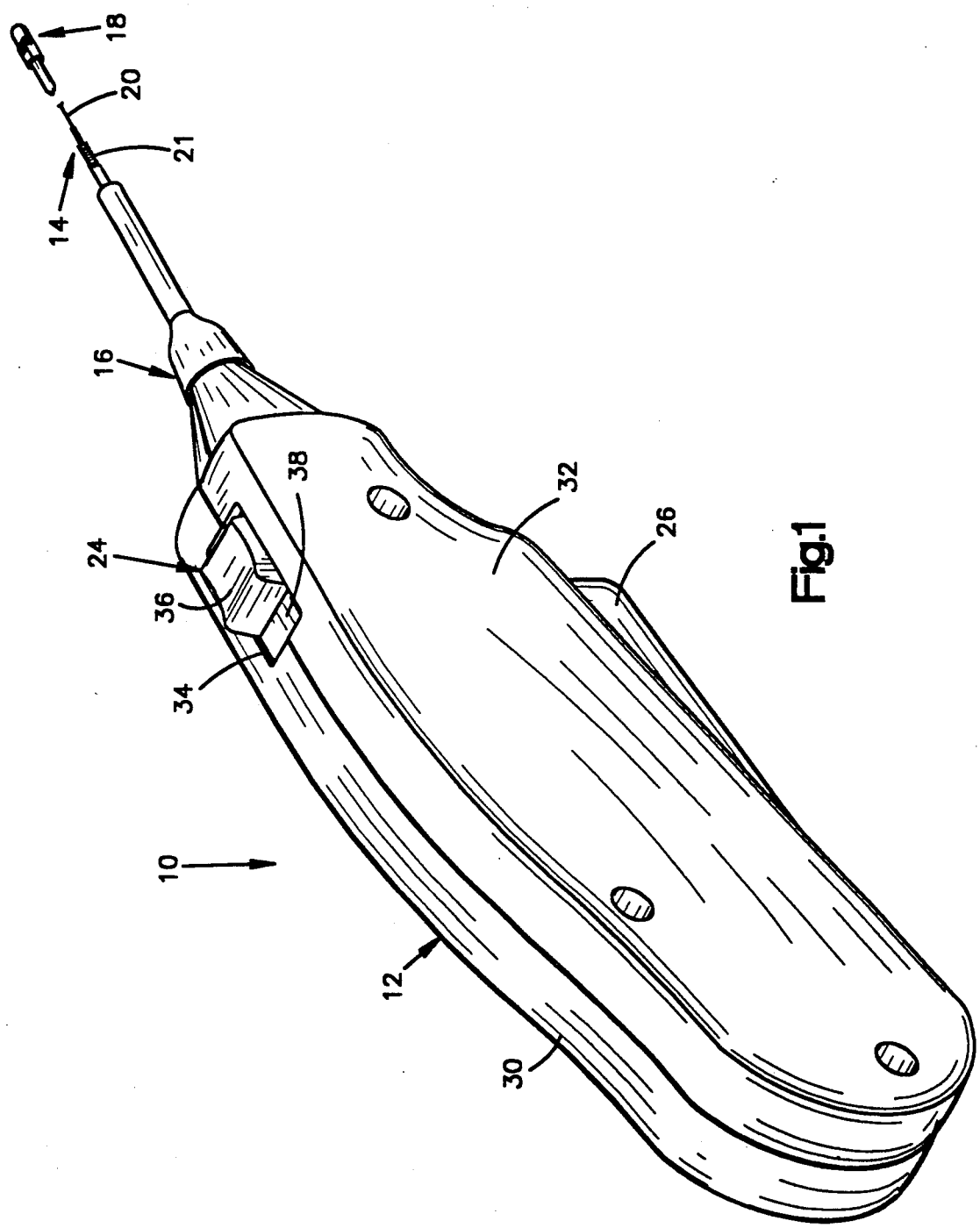
FIG. 1 is a perspective view of a biopsy forceps device constructed in accordance with the present invention.

Reference is now made to the drawings wherein the showings are for purposes of illustrating a preferred embodiment only and not for purposes of limiting same. As shown in the drawings, there is provided a biopsy forceps device 10 which includes a handle assembly 12 and an elongated flexible hollow body taking the form of a coil spring guide 14 which extends from the distal end 16 of the handle assembly to a forceps assembly 18. The guide 14 has a lumen extending throughout its length and the lumen slidably receives a control wire 20 which is connected at its distal end to the forceps assembly 18 and secured at its proximal end to a grip 22. The guide is surrounded by a plastic protective sleeve 21.

Figure 3:
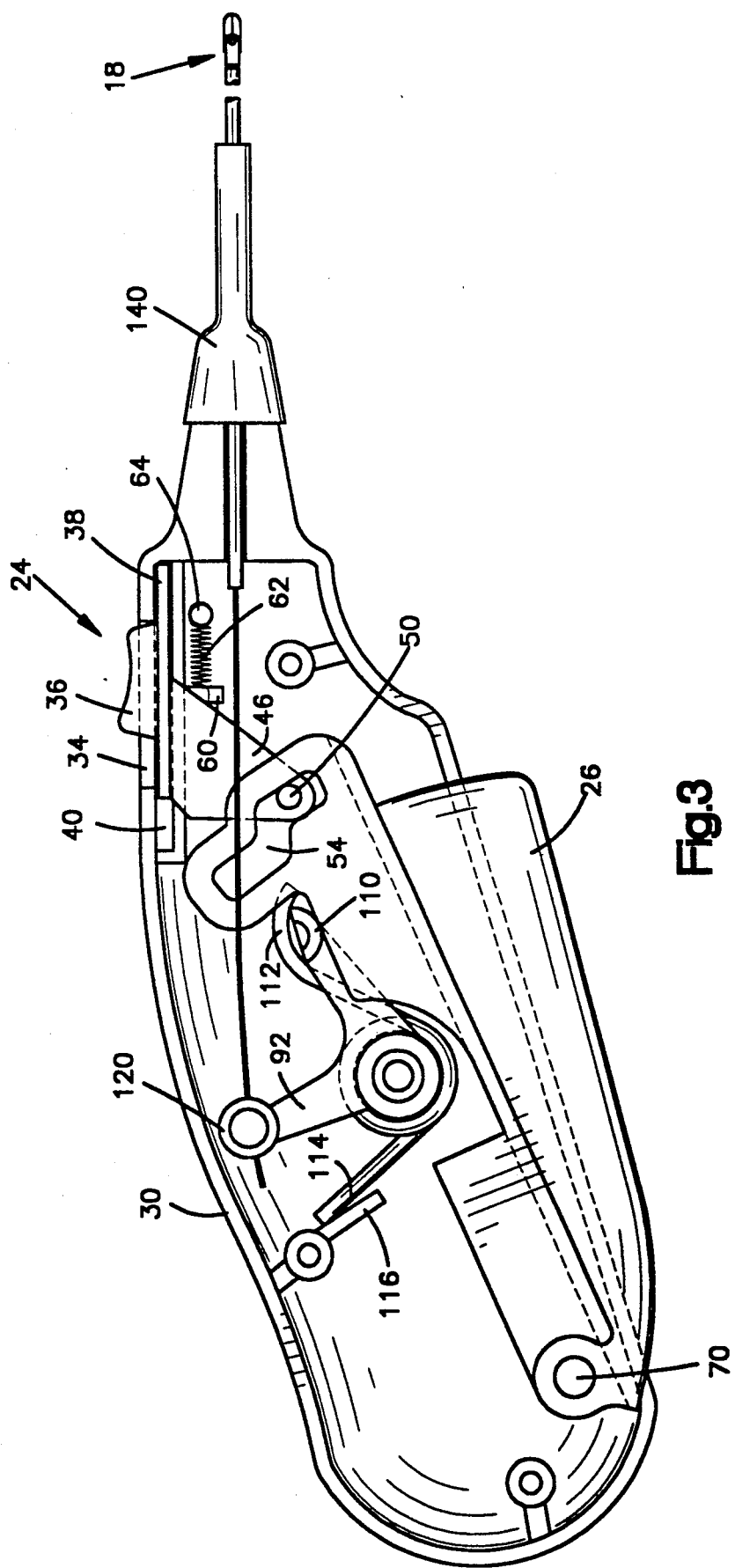
FIG. 3 is a sectional view of the device illustrated in FIGS. 1 and 2 and showing the forceps in a closed condition.
Figure 5:
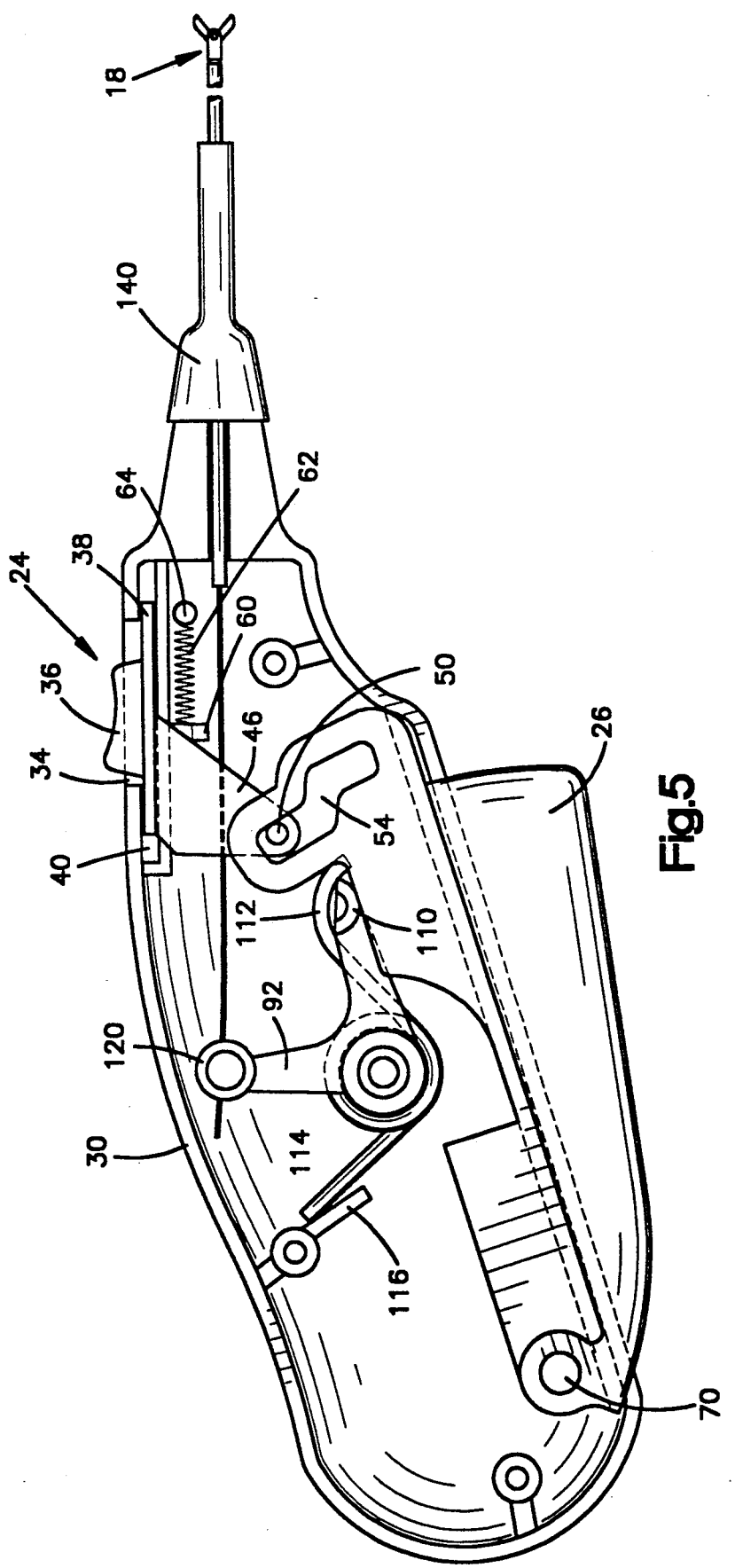
FIG. 5 is a view similar to that of FIGS. 3 and 4 but showing the operation when the forceps are in an open condition.

The grip 22, as will be brought out in greater detail hereinafter, displaces the control wire 20 from the proximal position, as shown in FIG. 3, forwardly to a distal position, as shown in FIG. 5, to thereby open the forceps assembly 18. As will be brought out in greater detail hereinafter, this action results from the operator engaging a trigger 24 with his thumb and pulling the trigger rearwardly from its distal position to its proximal position.

The handle 12 is of an in-line design and may be easily grasped by either hand of a physician with the thumb engaging the trigger 24 and with the fingers engaging a lever arm 26. The forceps are operated to an open condition by the physician placing his thumb on the trigger 24 and pulling back on the trigger until it locks in a proximal position. With the trigger in its proximal position, the physician may close the forceps by compressing the lever arm 26 up into the clamshell body of the handle assembly 12.

The handle assembly 12 resembles a clamshell body having a first clamshell half 30 and second clamshell half 32 which are hollowed out to receive and support the components to be described hereinbelow. The clamshell halves may be secured to each other as with suitable screws or by means of a snap fit. The distal end 16 of the handle assembly 12 is tapered in the distal direction and is provided with a passageway or lumen 31 which extends in an axial or in-line direction with the coil spring guide 14. This permits the proximal end of the coil spring guide 14 to be received by the lumen 31. The control wire 20 is slidably displaced within the lumen of guide 14 back and forth between its distal and proximal positions while opening and closing the forceps 18.

The handle assembly 12 is provided with a longitudinally extending opening 34 in its upper wall near the distal end thereof and a thumb button 36 of the trigger 24 extends upwardly and beyond the opening so that it may be easily engaged by the thumb of the operator. The thumb button 36 extends upward from a flat rectangular platform 38 and the longitudinal sides of the platform are received in tracks 40 located in the interior side walls in the cooperating clamshell halves 30 and 32 just below the opening 34. This permits the trigger 24 to slide back and forth between its distal and proximal positions. The trigger 24 is also provided with a pair of legs 44 and 46 which extend vertically downward from the underside of platform 38. At the lower end of leg 44 there is provided a transversely extending cam post 48. A similar cam post 50 extends transversely outward from the bottom of leg 46. These cam posts ride in a pair of cam tracks 52 and 54 located in the lever arm 26.

The trigger 26 has a rod-like post 60 which extends from the underside of platform 38 in a downward direction between legs 44 and 46. This post 60 (as best seen in FIG. 3) serves to anchor one end of a compression spring 62 with the other end of the compression spring being anchored to a rod-like post 64 which extends inwardly from a side wall of the clamshell half 30. This compression spring provides the resilient force that tends to keep the trigger 24 in its forward or distal position, as seen in FIG. 3.

Figure 2:
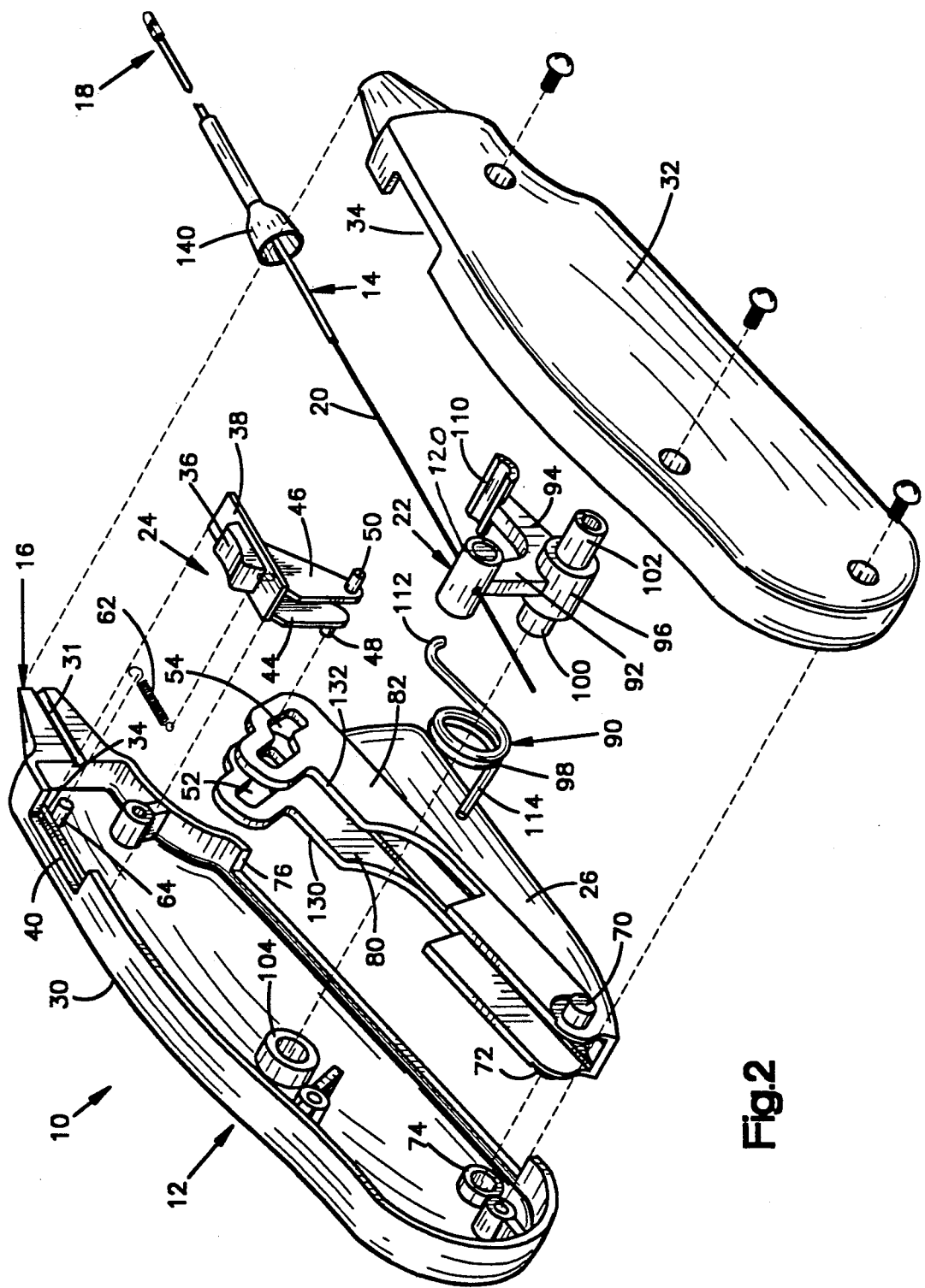
FIG. 2 is an exploded view showing various of the components employed in the embodiment illustrated in FIG. 1.

The lever arm 26 has a pair of pivot posts 70 and 72 which extend transversely outward from the arm at one end thereof. These pivot posts are received in a pair of facing pivot sleeves 74, of which only one is seen in FIG. 2, provided on the interior walls of clamshell halves 30 and 32. These pivot sleeves face inwardly toward the arm and have internal diameters sufficient to receive the posts 70 and 72 while permitting pivotal movement of the posts in the sleeves. Thus, post 72 is received within pivot sleeve 74 so that the arm 26 may pivot about an axis extending through the pivot post while the arm is displaced in an arcuate direction into and out of the interior of the handle assembly 12. For this purpose, the handle assembly 12 includes an elongated slot 76 which extends through the lower walls of clamshell halves 30 and 32 with the slot being of sufficient width and length to receive the lever arm 26 as it is pulled up into the interior when the operator compresses the lever arm up into the clamshell body.

The lever arm 26 has a somewhat wedge-shaped body with the apex thereof being provided with the pivot posts 70 and 72. In cross section, the lever arm is somewhat U-shaped defining a trough having a pair of upstanding side walls 80 and 82 which respectively contain the lever arm cam tracks 52 and 54. These cam tracks 52 and 54 are somewhat S-shaped.

A torsion spring 90 is employed for purposes of biasing the lever arm to its fully extended position corresponding with a forceps open condition as shown in FIG. 5. Also, this biases the grip 22 in its forward or distal position. This structure and the means for accomplishing the foregoing are described in detail hereinbelow.

The grip 22 takes the form of a V-shaped structure having a pair of legs 92 and 94 and having a transversely extending hub 96 at its apex. The hub 96 is of sufficient diameter to receive a pair of turns 98 of the spring 90 while permitting rotational movement between the hub and the turns 98. A pair of pivot posts 100 and 102 extend transversely from the hub 96 and these pivot posts are each received within a pivot sleeve 104 extending inwardly from the side walls of the clamshell halves 30 and 32 (only the pivot sleeve 104 of clamshell half 30 is visible in FIG. 2). The pivot post 100 is received within the pivot sleeve 104 such that the pivot post 100 may pivot or rotate within the sleeve 104.

Figure 4:
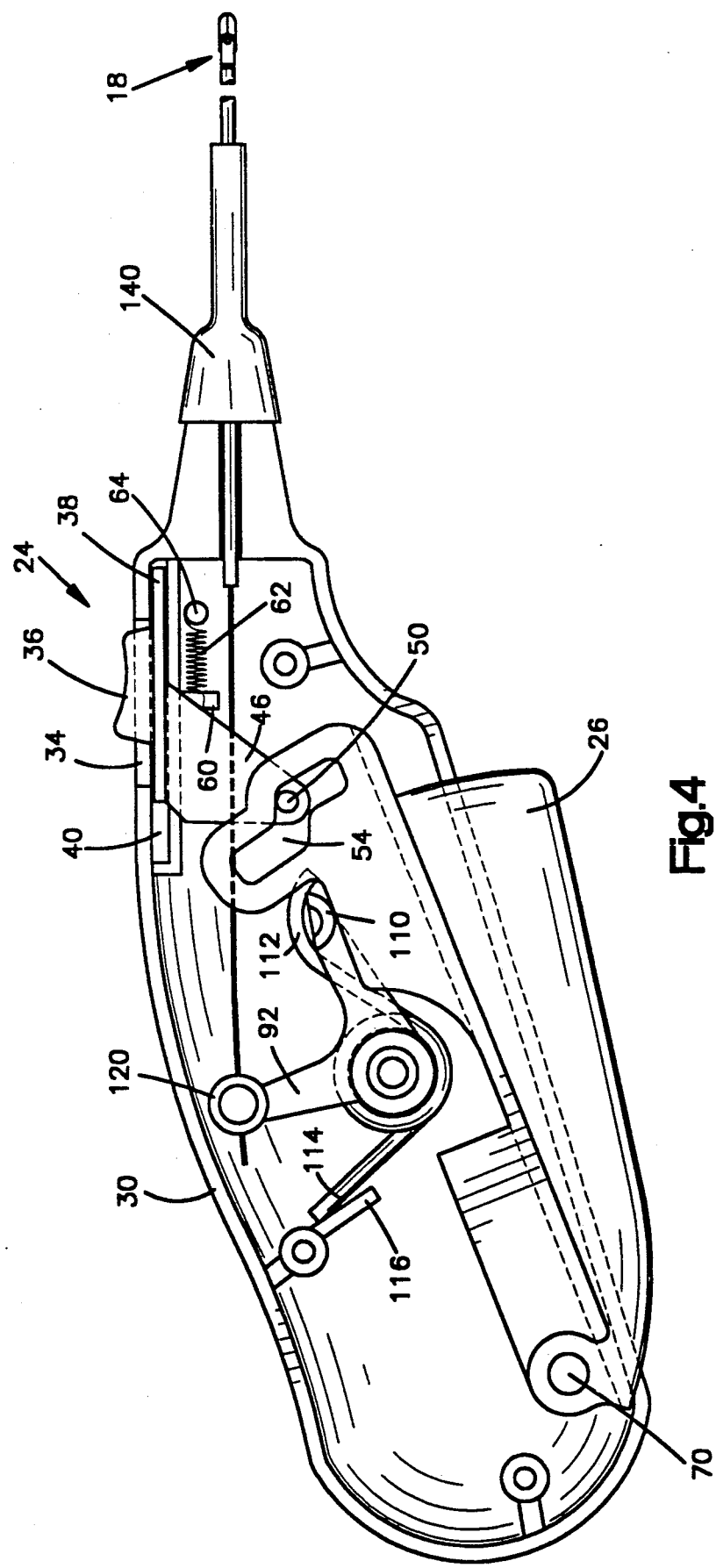
FIG. 4 is a sectional view similar to that of FIG. 3 but showing intermediate operation condition.

Leg 94 extending from the hub 96 carries at its end a transversely extending spring retaining member 110 which receives a hooked end 112 of spring 90, as is best seen in FIGS. 3, 4 and 5. The other end 114 of spring 90 bears up against a wall 116 extending inwardly from an inner side wall of the clamshell half 30. The other leg 92 of grip 22 has a wire gripping member 120 secured to the end of the leg. This wire gripping member 120 has an aperture therein for receiving a portion of the length of the control wire 20 and which is fastened to the gripping member 120 as with a set screw, not shown. The torsion spring 90 has its hooked end 112 hooked over the spring retaining member 110 of the grip 22. This forces member 110 to bear downwardly against the upper edges 130 and 132, respectively, of the lever arm side walls 80 and 82. With the other end 114 of the spring bearing against wall 116, this torsion spring biases the lever arm toward its fully extended position, shown in FIG. 5 and which corresponds with the forceps open condition. A protective plastic cover 140 extends over a portion of the distal end 16 of the handle as well as over a portion of the length of the coil spring guide 14.

In operation, the physician may grasp the handle assembly 12 in either hand and then place his thumb on the thumb button 36 and pull the button back, from its distal position to its proximal position. This action will cause the cam tracks 52 and 54 to ride down on the cam posts 48 and 50, respectively, as the lever arm pivots about its pivot posts 70 and 72 in a clockwise direction under the urging of the torsion spring 90. This action continues from the position as shown in FIG. 3, through an intermediate position, as shown in FIG. 4, and to a final position, as shown in FIG. 5 at which the forceps assembly is in its open condition. During this operation, the lever arm 26 pivots from its fully retracted position, as shown in FIG. 3, to an intermediate position, as shown in FIG. 4, and then to its fully extended position, as shown in FIG. 5. During this operation, the grip 22 is biased by the spring 90 so as to pivot in a clockwise direction causing the control wire 20 to be displaced in a distal direction sufficient to cause the forceps assembly to be actuated into its open condition. The forceps assembly is now maintained in its open condition by the resilient force exerted by spring 90.

To close the jaws, the physician compresses the lever arm 26 up into the clamshell body from the position as shown in FIG. 5 through an intermediate position as shown in FIG. 4 to the lever arm fully retracted position of FIG. 3. During this operation, the trigger 24 is released from its proximal position, as shown in FIG. 5, to travel forwardly through an intermediate position, as shown in FIG. 4, to its distal position, as shown in FIG. 3, as the platform 38 slides forwardly in a distal direction in the guides 40 within the handle (see FIG. 3). During this operation, the cam posts 48 and 50 ride in the lever arm cam tracks 52 and 54 from the position shown in FIG. 5 through that as shown in FIG. 4 and then to the position as is shown in FIG. 3 with the lever arm 26 being fully retracted into the clamshell body. As the lever arm 26 is compressed into the clamshell body, the grip 22 pivots in a counterclockwise direction about its pivot axis against the resisting force of the spring 90 during which the control wire 20 is displaced from its distal position to its proximal position sufficient to cause the forceps assembly 18 to a closed condition. In this condition, the trigger assembly 24 is held in its distal position by the force exerted by compression spring 62. The biopsy forceps is now in condition to repeat the foregoing operation by the physician applying his thumb to pull back on the thumb button on the trigger 24 in order to open the forceps assembly.

Although the invention has been described in conjunction with a preferred embodiment, it is to be appreciated that various modifications may be made without departing from the spirit and scope of the invention as defined by the appended claims.

Having described the invention, the following is claimed:

1. A biopsy forceps device comprising:
   a handle;
   an elongated flexible hollow-body portion having a lumen extending therethrough, and having a proximal end and a distal end;
   a forceps assembly coupled to the distal end of said body portion, and including a pair of forceps;
   control wire means having proximal and distal ends, and extending through the lumen in said body portion and coupled at its proximal end to said handle and at its distal end to said forceps assembly;
   trigger means mounted to said handle for slidable movement relative thereto between a proximal position and a distal position;
   gripping means for gripping the proximal end of said control wire means and movable between first and second positions for respectively moving said control wire means between a forceps open condition and a forceps closed condition;
   first means for resiliently biasing said gripping means toward its first position corresponding with said forceps open condition;
   actuatable lever arm means for engaging and moving said gripping means from its said first position to its said second position against the resilient biasing action of said first means; and
   releasable locking means carried by said trigger means and said lever arm means for locking said gripping means in said second position corresponding with said forceps closed condition so long as said trigger means is in its distal position.

2. A biopsy forceps device as set forth in claim 1 including second means for resiliently biasing said trigger means toward its said distal position.

3. A biopsy forceps device as set forth in claim 2 including a thumb actuatable means carried by said trigger means for displacing said trigger means from its said distal position to its said proximal position and releasing said locking means permitting said gripping means to be displaced by said first means to its first position corresponding with said forceps open condition.

4. A biopsy forceps device as set forth in claim 3 wherein said trigger means carries camming means and wherein said lever arm means carries a cam track in engagement with said camming means for locking said gripping mean in said second position so long as said trigger means is in its distal position.

5. A biopsy forceps device as set forth in claim 4 wherein said lever arm means is pivotally mounted to said handle for pivotal movement between an extended position and a retracted position respectively corresponding with said first and second positions of said gripping means.

6. A biopsy forceps device as set forth in claim 5 wherein said gripping means is pivotally mounted to said handle for pivotal movement between its said first and second positions.

7. A biopsy forceps device as set forth in claim 6 wherein said handle is an elongated hollow body having an elongated slot for receiving portions of said lever arm means as it is displaced from its fully retracted position within said handle and its fully extended position.

8. A biopsy forceps device as set forth in claim 7 wherein said handle is pivotally mounted to the interior walls within said handle.

9. A biopsy forceps device as set forth in claim 7 wherein said body has a second elongated slot through which said thumb actuatable means protrudes.

10. A biopsy forceps device a set forth in claim 1 wherein said handle is an elongated hollow body and wherein said gripping means is pivotally mounted within said body to the interior walls thereof for movement within said body between said first and said second positions, said handle having a distal end having a lumen therethrough for slidably receiving a portion of the length of said control wire means.

* * * * *